United States Patent [19]

Fiala

[11] Patent Number: Plant 6,942

[45] Date of Patent: Jul. 25, 1989

[54] CRABAPPLE TREE NAMED AMBERINA

[75] Inventor: John L. Fiala, Medina, Ohio

[73] Assignee: Yoder Brothers, Inc., Barberton, Ohio

[21] Appl. No.: 213,604

[22] Filed: Jun. 30, 1988

[51] Int. Cl.[4] ..... A01H 5/00

[52] U.S. Cl. ..... Plt./34

[58] Field of Search ..... Plt./34

*Primary Examiner*—James R. Feyrer

*Attorney, Agent, or Firm*—Foley & Lardner, Schwartz, Jeffery, Schwaab, Mack, Blumenthal & Evans

[57] ABSTRACT

An ornamental flowering crabapple tree named Amberina, having disease resistant deep green leaves that change to bright gold in autumn. The cultivar produces firm, glossy, small bright red berries that maintain themselves on the tree for the entire winter. Rose-pink buds open to pure white fragrant blossoms. The cultivar roots easily as a soft wood cutting.

4 Drawing Sheets

The present invention comprises a new and distinct cultivar of crabapple tree, botanically known as *Malus zumi,* and hereinafter referred to by the cultivar name Amberina.

The new cultivar, discovered by the inventor in 1972, resulted from a controlled cross by applicant of seed parent *Malus zumi* 'Christmas Holly' with pollen parent (*Malus zumi* #243×*Malus zumi* #768), in Medina, Ohio.

Asexual reproduction in the form of softwood cuttings and summer chip budding by applicant in Medina, Ohio has demonstrated that the combination of characteristics as herein disclosed for the new cultivar are firmly fixed and are retained through successive generations of asexual reproduction.

Amberina has not been observed under all possible environmental conditions. The phenotype may vary significantly with variations in environment such as temperature, light intensity, day length, available soil moisture, soil nutrients and $p^H$ level.

The following observations, measurements, and comparisons describe trees grown at Klehm Nursery, Barrington, Ill., under conditions approximating those generally used in commercial practice.

The following repeatedly observed traits and characteristics of Amberina, in combination, distinguish this crabapple tree as a new and distinct cultivar for ornamental and landscape use.

1. Amberina has a strong, upright growth habit, reaching a mature height of about 10 feet.
2. The cultivar's disease resistant, deep green leaves change to bright gold in autumn.
3. Amberina produces bright red berries that maintain themselves on trees for the entire winter.
4. Amberina abundantly flowers as a young tree, producing pink to rose colored buds that open to pure white, flagrant blooms.
5. Amberina roots easily as a soft wood cutting.

Of the many commercial crabapple trees known to the inventor, the most similar in comparison to Amberina is the species *Zumi calocarpa.* In comparison to *Zumi calocarpa* cultivars, Amberina has much better winter fruit retention, more abundant blossoms, and foliage that is more resistant to summer diseases.

The accompanying color photographic drawings show typical characteristics of Amberina, with colors being as true as possible with illustrations of this type.

Sheet 1 is a photograph of Amberina in perspective view.

Sheet 2 is a closeup photograph of a branch of Amberina in the bud stage.

Sheet 3 is a photograph of a branch of Amberina, showing buds in varying stages of opening.

Sheet 4 illustrates a branch of Amberina bearing mature fruit.

In the following detailed description of the cultivar, color references are made to The Royal Horticultural Society Colour Chart (R.H.S.).

TREE

Origin: Seedling.

Parentage:

*Seed parent.*—*Malus zumi* 'Christmas Holly'.

*Pollen parent.*—(*Malus zumi* #243×*Malus zumi* #768).

Classification:

*Botanic.*—*Malus* ×cv Amberina.

*Commercial.*—Ornamental flowering crabapple.

Propagation: Chip budding, bench grafting, softwood cuttings.

Branches: Rather stout and upright.

Height: Reaches an average of 10 feet, at 15 years.

Growth habit: Upright.

Fruit bearing habit: Annual, heavily fruited, persistant retention over winter.

Foliage:

*Size of leaf.*—2–2.25" long by 1–1.25" wide.

*Shape of leaf.*—Elliptical.

*Margin.*—Entire.

FLOWERS

Buds:

*Color.*—Approximately 39B-C, although color varies greatly on each bud and state of maturity.

*Size.*—Small.

*Shape.*—Ovoid.

Form: Multiple clusters (5 to 10).

Size: 1.5 to 2.0" wide.

Date of first bloom: Normally May 10–15.

Date of full bloom: Normally May 15–20.

Color: Mature, fully open blossoms are pure white, as evident from the perspective view of the entire tree.

FRUIT

Date of maturity: Annually, October 15.
Shape: Round and small ($\frac{1}{4}$ to 5/16″ in diameter).
Hardness: Very firm and persistent.
Form: Clusters of five to six.
Markings: Clear, with a shiny gold overlay.
Skin: Attractively shiny and glistening.
Color: 44A-B.
Keeping quality: Excellent.

Bruise resistance: Very resistant.
Insect and disease resistance: Very resistant to the common ornamental crabapple disease apple scab, cedar-apple rust, fire blight, fog-eye leaf spot, and powdery mildew.
Primary use: Ornamental and landscape usage.

I claim:

1. A new and unique flowering crabapple tree named Amberina, as illustrated and described.

* * * * *

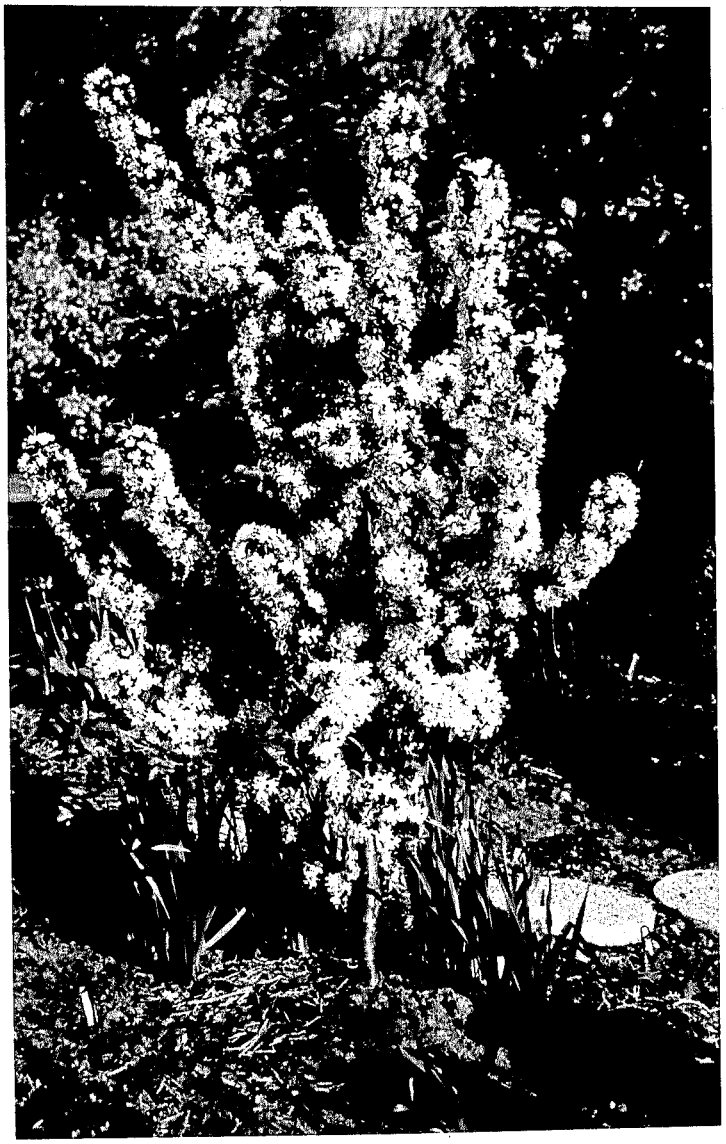

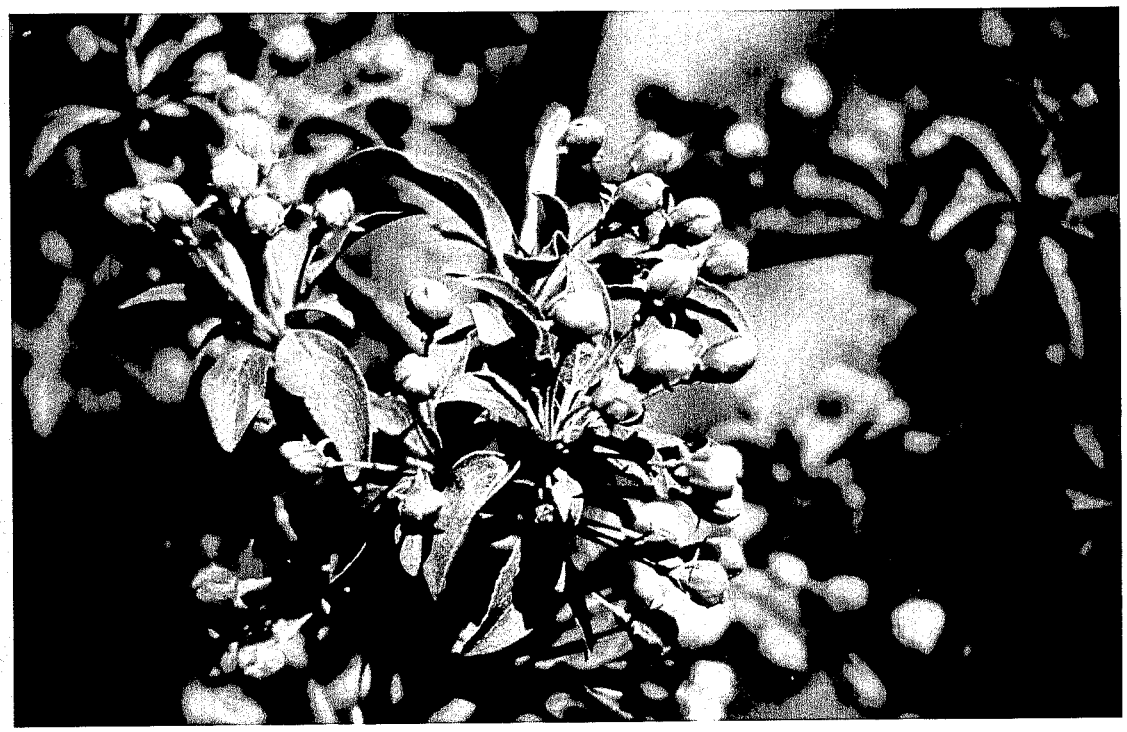

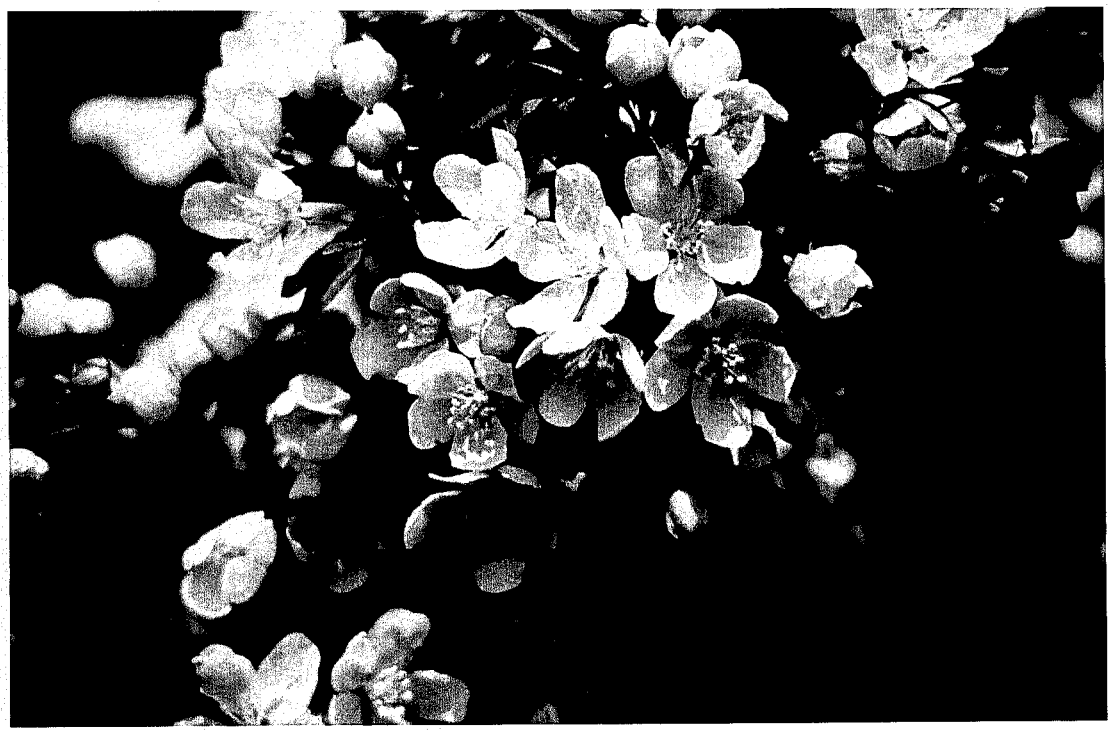

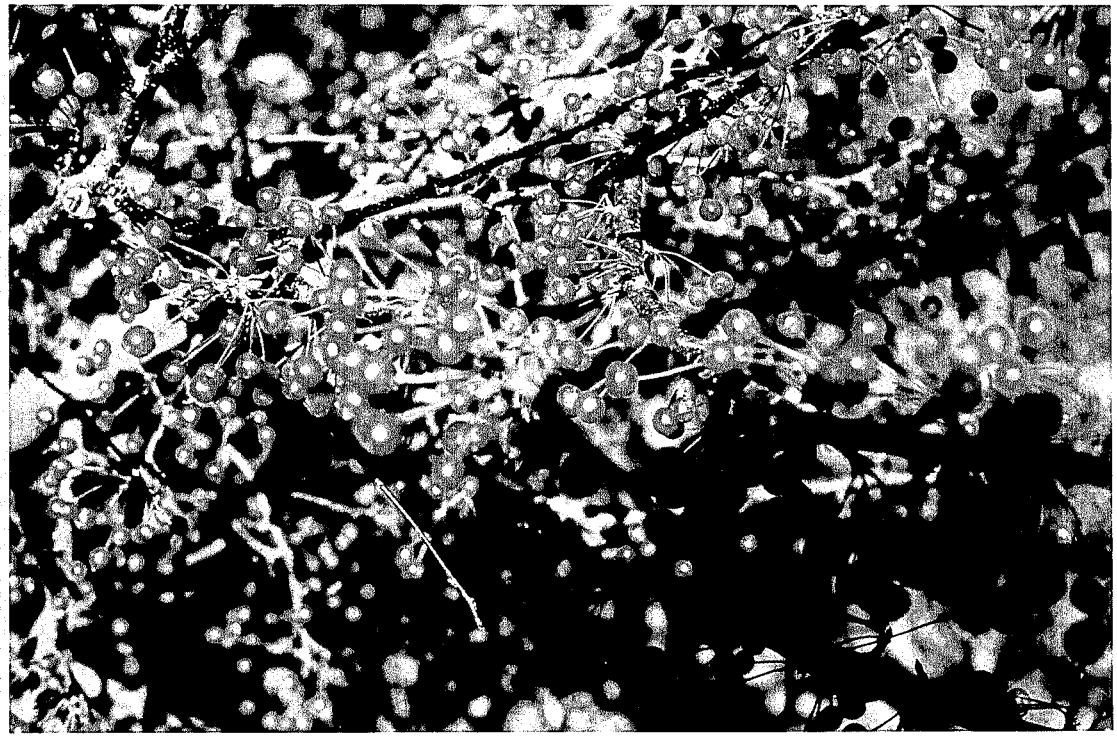

UNITED STATES PATENT AND TRADEMARK OFFICE

CERTIFICATE OF CORRECTION

PATENT NO. : Plant No. 6,942

DATED : July 25, 1989

INVENTOR(S) : John L. Fiala

It is certified that error appears in the above—identified patent and that said Letters Patent is hereby corrected as shown below:

TITLE PAGE

In the heading, at line (73), the Assignee should read:

"Chas. Klehm & Son, South Barrington, Illinois"

Signed and Sealed this

Twenty-seventh Day of April, 1993

*Attest:*

MICHAEL K. KIRK

*Attesting Officer*

*Acting Commissioner of Patents and Trademarks*